United States Patent [19]

Holtkamp, Sr.

[11] Patent Number: Plant 6,601

[45] Date of Patent: Feb. 14, 1989

[54] AFRICAN VIOLET PLANT NAMED VANESSA

[75] Inventor: Reinhold Holtkamp, Sr., Isselburg, Fed. Rep. of Germany

[73] Assignee: Gesellschaftsvertrag uder die Erfindergemeinschaft "Optimara", Rees Haffen, Fed. Rep. of Germany

[21] Appl. No.: 55,860

[22] Filed: Jun. 1, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

An African violet plant named Vanessa, characterized by its violet-shaped, pink flowers with slightly ruffled edges; strong upright wire-like flower stems; a tight bouquet free above the leaves; profuse flowering; vigorous growth habit; oval to heart-shaped leaves; and long lasting, non-dropping flowering habit.

1 Drawing Sheet

The present invention comprises a new and distinct cultivar of African violet plant, botanically known as *Saintpaulia ionantha,* and hereinafter referred to by the cultivar name Vanessa.

The new cultivar was referred to during the breeding and selection process by the designation I17/5, and is a product of a planned breeding program. The new cultivar was originated from a cross made by applicant in a controlled breeding program in Haffen, Federal Republic of Germany. The female, or seed parent was a cultivar designated F38/6. The male, or pollen parent was a cultivar designated E29/19 Pink.

Vanessa was discovered and selected by me as a flowering plant within the progeny of the stated cross in a controlled environment in Haffen, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Vanessa has not been observed under all possible environmental conditions. The phenotype may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Vanessa which in combination distinguish this African violet as a new and distinct cultivar:

1. Violet-shaped dark pink flowers with slightly ruffled edges.
2. First flash of flowers forms a tight bouquet free above the dark green leaves.
3. Each plant has 7–9 or more upright flower stems, each of which carries 10–12 or more flowers.
4. Profuse flowering.
5. Seed capsule pushes slightly through.
6. Vigorous power,
7. Plant saleable 9–10 weeks after potting.
8. Long-lasting, non-dropping single flowers.

9. After maturity, the flowers dry off and remain on the peduncle without becoming infected by botrytis.
10. Strong, upright wire-like flower stems.
11. Some flowers have 1 to 2 additional flower petals.
12. The pink flower color intensifies towards the center of the blossoms.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors or ordinary significance are referred to. Color values were taken under natural light conditions at approximately 2:00 p.m. in Nashville, Tenn. Under cooler growing conditions and more intensive lighting, the pink color becomes more intense.

Botanical classification: *Saintpaulia ionantha,* Ramat., cv. Vanessa.

Parentage:

*Male parent.*—E29/19 Pink.

*Female parent.*—F38/6.

Propagation: The new cultivar holds its distinguishing characteristics through successive propagations by leaf cuttings and by division of shoots.

Plant: From 9–11 cm tall when grown in pots, and approximately 22–25 cm in diameter when fully grown. The growth rate is vigorous.

*Leaves.*—Shape: Oval to heart-shaped. Diameter: 55–70 mm. Texture: Soft, velvety. Aspect: Medium green, slightly hairy, shiny. Ribs and veins: Upperside visible, underside well pronounced, light green with increasingly more purple touch towards the petiole; purplish in between the leaves. Color (upper side): Darker than violet green 147A. Color (under side): Yellow green 148D. Petioles: Purplish to brownish, hairy.

*Flowers.*—Buds: Green with purplish touch, ball-shaped, 6–8 mm before opening. Sepals: Five (5) in number, brownish-green. Calyx: Funnel-shaped. Aspect: Spear-shaped, hairy. Peduncle: Strong, upright, brownish, hairy.

*Individual flowers.*—Size: 35 to 40 mm. Shape: Single, violet-shaped, slightly wavy with slightly frilled edge. Color (upper side): Red 55 between C and D, somewhat darker toward the center. Color (under side): Red 49D. Borne: Each flower stem carries 10–12 and more flowers on strong, upright wire-like peduncles that are free standing above the leaves. Corolla: Compact flower head formed on strong upright peduncles free standing above the leaves; 3 large petals; 2 slightly smaller. Flowering habit: Flowers 8–9 weeks after potting.

*Reproductive organs.*—Stamens: Two (2) in number. Anthers: Two composed of 4 cells, seed capsule pushes slightly through. Filaments: 4 mm, purplish green. Pollen Color: Yellow 7A Styles: 6 mm pink, base of ovary light green.

*Roots.*—Normally developed, white when young, turning slightly brownish when older.

Disease resistance: Good.

General observations: Vanessa is a very attractive, vigorous and floriferous grower with medium to dark green leaves and pink single violet-shaped flowers.

Seven to nine weeks after potting, the plant has developed 7–9 strong stems with 10–12 flowers with a slightly frilled edge. The center of the flowers is darker, especially on the 2 smaller petals. Occasionally, 2–3 additional petals develop on some flowers, giving the plant a semi-double look. The long-lasting, non-dropping flowers are on strong peduncles which form a nice bouquet that is free-standing above the leaves.

I claim:

1. A new and distinct cultivar of African violet named Vanessa, as described and illustrated, and particularly characterized by its violet-shaped, pink flowers with slightly ruffled edges; strong upright wire-like flower stems; a tight bouquet free above the leaves; profuse flowering; vigorous growth habit; oval to heart-shaped leaves; and long lasting and non-dropping flowering habit.

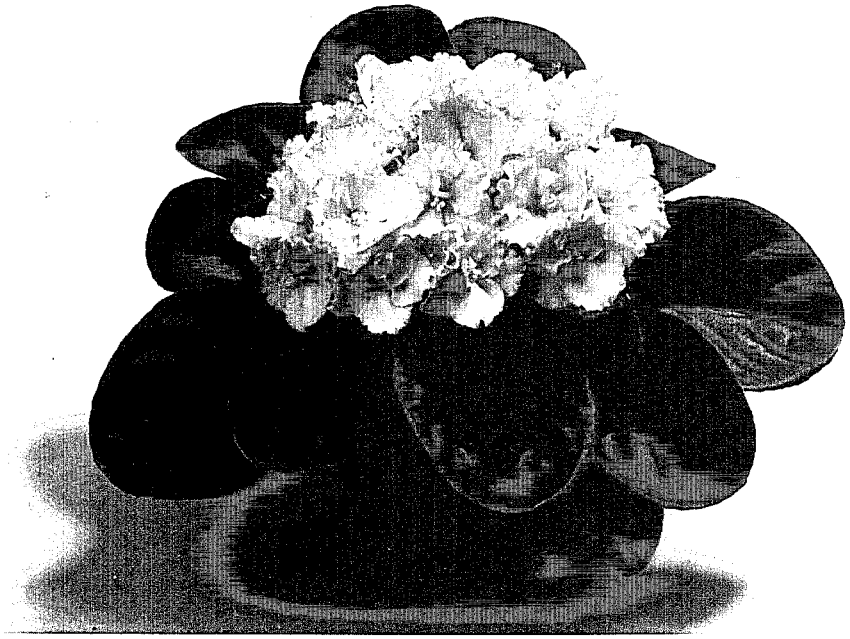

* * * * *